United States Patent
Kimoto et al.

(10) Patent No.: US 11,000,453 B2
(45) Date of Patent: May 11, 2021

(54) ORGANIC-INORGANIC COMPOSITE FILLER HAVING MANY REACTION GROUPS ON SURFACE AND DENTAL CURABLE COMPOSITION COMPOUNDED THEREWITH

(71) Applicant: SHOFU INC., Kyoto (JP)

(72) Inventors: Katsuya Kimoto, Kyoto (JP); Shunsuke Miyata, Kyoto (JP); Hideto Kasaba, Kyoto (JP)

(73) Assignee: SHOFU INC., Kyoto (JP)

( * ) Notice: Subject to any disclaimer, the term of this patent is extended or adjusted under 35 U.S.C. 154(b) by 0 days.

(21) Appl. No.: 15/435,506

(22) Filed: Feb. 17, 2017

(65) Prior Publication Data

US 2017/0231872 A1 Aug. 17, 2017

(30) Foreign Application Priority Data

Feb. 17, 2016 (JP) .............................. JP2016-027504

(51) Int. Cl.
| | | |
|---|---|---|
| *A61K 6/76* | (2020.01) | |
| *A61K 6/16* | (2020.01) | |
| *A61K 6/60* | (2020.01) | |
| *A61K 6/62* | (2020.01) | |
| *A61K 6/64* | (2020.01) | |
| *A61K 6/70* | (2020.01) | |
| *A61K 6/889* | (2020.01) | |

(52) U.S. Cl.
CPC ................. *A61K 6/76* (2020.01); *A61K 6/16* (2020.01); *A61K 6/60* (2020.01); *A61K 6/62* (2020.01); *A61K 6/64* (2020.01); *A61K 6/70* (2020.01); *A61K 6/889* (2020.01)

(58) Field of Classification Search
CPC .... A61K 6/0265; A61K 6/0088; A61K 6/007; A61K 6/0047
See application file for complete search history.

(56) References Cited

U.S. PATENT DOCUMENTS

| | | | |
|---|---|---|---|
| 6,620,861 B1 | 9/2003 | Nakatuka et al. | |
| 9,132,068 B2 * | 9/2015 | Toriyabe | A61K 6/0091 |
| 9,526,667 B1 * | 12/2016 | Wang | A61H 1/0229 |
| 9,526,677 B2 * | 12/2016 | Sadakane | A61K 6/0073 |
| 2016/0030299 A1 * | 2/2016 | Sadakane | A61K 6/0073 |
| | | | 523/116 |

FOREIGN PATENT DOCUMENTS

| | | |
|---|---|---|
| EP | 1 101 484 | 5/2001 |
| JP | 2001-288232 | 10/2001 |
| JP | 2003-95836 | 4/2003 |
| JP | 2010-229420 | 10/2010 |
| JP | 2012-121814 | 6/2012 |
| JP | 2012-180310 | 9/2012 |

OTHER PUBLICATIONS

Van Landuyt et al., "Systematic review of the chemical composition of contemporary dental adhesives", ScienceDirect, Biomaterials, vol. 28 (2007), pp. 3757-3785.
Extended European Search Report dated Oct. 12, 2017 in corresponding European Patent Application No. 17156647.4.
Office Action dated Jul. 24, 2018 in corresponding European Patent Application No. 17156647.4.
Office Action dated Dec. 28, 2020 in corresponding Japanese Patent Application No. 2017-027486 with English-language translation.

* cited by examiner

*Primary Examiner* — Sanza L. McClendon
(74) *Attorney, Agent, or Firm* — Wenderoth, Lind & Ponack, L.L.P.

(57) ABSTRACT

To provide an organic-inorganic composite filler containing; a polymerizable monomer (a) having at least one functional group selected from the group consisting of —OH group, —NH— group, and —NH$_2$ group, a polymerizable monomer (b) having no functional group selected from the group consisting of —OH group, —NH— group, and —NH$_2$ group, a polymerization initiator (c), an inorganic filler (d), and a silane compound (e) which generates —OH group by hydrolysis.

21 Claims, No Drawings

ORGANIC-INORGANIC COMPOSITE FILLER HAVING MANY REACTION GROUPS ON SURFACE AND DENTAL CURABLE COMPOSITION COMPOUNDED THEREWITH

This application is based on and claims the benefit of priority from Japanese Patent Application Serial No. 2016-027504 (filed on Feb. 17, 2016), the contents of which are hereby incorporated by reference in their entirety.

BACKGROUND OF THE INVENTION

Field of the Invention

The present disclosure relates to an organic-inorganic composite filler suitable for using as a filler in a dental curable composition such as a dental filling composite resin, a dental adhesive, a dental abutment construction material, a dental surface coating material, a pit and fissure plugging material, a dental manicure material, a dental crown restoration material, an artificial tooth material and the like, and the dental curable composition contains the organic-inorganic composite filler of the present disclosure.

Description of the Related Art

In the dental clinical field, a dental filling composite resin is used to esthetically and functionally restore a lost portion of a tooth caused by dental caries, tooth fracturing, etc. The dental filling composite resin is generally prepared by mixing a resin matrix including several types of polymerizable monomers, various filling materials such as an inorganic filler, an organic-inorganic composite filler, etc., and a polymerization catalyst with each other into a uniform paste form.

Requirements demanded to a dental filling composite resin include mechanical strength durable to the high occlusal pressure, a color tone and transparency similar to a natural tooth, low polymerization shrinkage for preventing the generation of the contraction gap in polymerizing and curing, a high surface luster by polishing and gloss maintainability, a high X-ray contrast property facilitating a prognosis diagnosis, a sustained-release property of various ions such as fluorine to strengthen the tooth and to prevent secondary caries, and excellent operability for a dentist to execute a filling operation. In addition, especially in recent years, the aesthetic demand on the teeth by patient have increased and the needs for a dental filling composite resin having a surface luster by polishing and gloss maintainability tends to increase.

It is possible to impart an excellent surface luster and gloss maintainability by making an average particle diameter of a filler compounded in a dental filling composite resin smaller. However, because the smaller the average particle diameter of the filler becomes, the larger the specific surface area becomes, there is a problem that the filler filling amount decreases. As a result, there have been problem that the burden and the pain to the technician and the patient are increased by lengthening chair-time because the operability is lowered by increasing the viscosity of the paste, in addition to the problem that the surface hardness is decreased and the polymerization volume shrinkage is increased in the dental filling composite resin. In order to overcome these disadvantages, a filler commonly called an organic-inorganic composite filler has been proposed. This organic-inorganic composite filler is a composite filler obtained by previously mixing an inorganic filler having a small average particle size and a polymerizable monomer, polymerizing and curing the mixed material, and then pulverizing the polymerized product.

Aesthetic characteristics such as an excellent surface luster and glossiness after final polishing are exhibited by compounding the organic-inorganic composite filler in the dental filling composite resin. However, the organic-inorganic composite filler has a disadvantage that the surface treatment effect by the silane coupling agent is hard to be effective and wettability with respect to the resin is poor. Therefore, the dental filling composite resin compounded with the organic-inorganic composite filler has a serious problem in mechanical strength or operability. The reason why the effect of surface treatment by the silane coupling agent on the organic-inorganic composite filler is not effective is considered as follows.

In general, various surface treatments have been performed for the purpose of improving the wettability of various fillers with respect to the resin and for improving the mechanical strength, abrasion resistance and the like of the composition, and a silane coupling agent has been mainly used as a surface treatment agent in the dental field. This silane coupling agent works on a silanol group which is hydrophilic and presents on the surface of an inorganic filler, to form a covalent bond, thereby rendering the surface of the filler hydrophobic and exhibiting an effect of improving wettability with respect to the resin. However, since the surface of the organic-inorganic composite filler is mostly covered with the cured resin matrix, there are few inorganic fillers exposed on the surface. In addition, the inorganic filler is often subjected to surface treatment in advance using a silane coupling agent or the like in preparing the organic-inorganic composite filler. Therefore, even if the inorganic filler is exposed on the surface of the organic-inorganic composite filler, because unreacted silanol groups are hardly remained, the surface treatment effect on the organic-inorganic composite filler may not be sufficiently exhibited. Furthermore, since the silane coupling agent is merely physically adsorbed on the surface of the resin matrix of the organic-inorganic composite filler, the silane coupling agent tends to desorb from the surface of the filler. As a result, the wettability of the organic-inorganic resin composite filler with respect to the resin decreases over time to cause a change in the paste properties, thus the operability is deteriorated.

Therefore, for the purpose of improvement of the mechanical characteristic and the operability in the organic-inorganic compound filler, some inventions are disclosed.

Japanese Unexamined Patent Application Publication No. 2001-288232 discloses an organic-inorganic composite filler in which a double bond remains on the surface of the filler by using a trifunctional polymerizable monomer in the organic-inorganic composite filler. However, although the purpose of the organic-inorganic composite filler is to improve the mechanical strength, the effect is still insufficient.

Japanese Unexamined Patent Application Publication No. 2003-95836 discloses an organic-inorganic composite filler subjected to surface treatment with mono (meth) acrylate having a cyclic ether structure in the molecule. By using the mono (meth) acrylate having this specific molecular structure to surface treatment of the surface of the organic-inorganic composite filler, the specific molecular structure acts on the resin matrix on the surface of the organic-inorganic composite filler. In addition, since the mono (meth) acrylate having this specific molecular structure has an unsaturated double bond, it can be copolymerized with the resin of the dental restorative composition. As a result, because the inter face bonding between the organic-inorganic composite filler and the resin is strengthened, a dental restorative material having high mechanical strength may be obtained. However, since the surface treatment agent having this specific molecular structure acts only on the resin matrix on the surface of the organic-inorganic composite filler and does not exhibit a surface treatment effect on the inorganic filler exposed on the surface. Therefore, it is not possible to uniformly surface-treating the inorganic composite filler.

Japanese Unexamined Patent Application Publication No. 2010-229420 discloses an organic-inorganic composite filler in which the surface is coated with a silane compound and/or a low condensate of a silane compound. This filler has good polishing properties and may impart excellent mechanical strength, durability and stable operability of the paste without impairing properties such as a surface luster and glossiness after polishing. However, in the preparation of this filler, firstly an inorganic filler and a resin are uniformly mixed, then the resultant mixture is cured by heating and then pulverized and classified to obtain the organic-inorganic composite filler. Further, the organic-inorganic composite filler is dissolved in a solvent such as ethanol or the like, and is added with a low condensate of the silane compound by dropping in stirring-mixing condition to react. Then, the solvent is distilled off and heat treatment and disintegration are performed. Therefore, there is a problem that the preparation process is complicated.

As described above, there have been no organic-inorganic composite filler which may exhibit an excellent surface luster and glossiness after polishing, high transparency, and excellent mechanical strength and operability in a dental curable composition containing the organic-inorganic composite filler, and may be prepared easily without a complicated filler preparing process.

Conventionally, a dental curable composition containing an organic-inorganic composite filler exhibits excellent aesthetic properties such as a surface luster and glossiness after finish polishing, a low polymerization volume shrinkage and the like. However, there is a problem that mechanical strength is low and operability is decreased by change in paste properties over time. The major cause of this problem is that the silane coupling agent is physically adsorbed because there is little reaction group which may react with the silane coupling agent, on the surface of the organic-inorganic composite filler.

SUMMARY OF THE INVENTION

Technical Problem

Accordingly, an object of the present disclosure is to provide an organic-inorganic composite filler having a large number of reactive groups capable of efficiently reacting with a silane coupling agent for improving wettability with respect to a resin. Furthermore, another object of the present disclosure is to provide a dental curable composition which may exhibit high mechanical strength and excellent operability due to stable paste properties by compounding the organic-inorganic composite filler of the present disclosure into a dental curable composition such as a dental crown material, a filling material, a prosthetic material and an adhesive material used in the dental field, in addition to the various features of the conventional dental curable composition brought by the conventional organic-inorganic composite filler.

Solution to Problem

The present inventors have made intensive studies in order to solve the above problem, and as a result, have found that the organic-inorganic composite filler containing a polymerizable monomer having a specific functional group, a polymerizable monomer not having a specific functional group, an inorganic filler, a polymerization initiator, and a silane compound which generates an —OH group by hydrolysis, has many reaction sites on the surface, in which reaction sites may be efficiently react with a silane coupling agent, and the wettability with respect to the resin is remarkably improved by surface treatment of the organic-inorganic composite filler with the silane coupling agent, leading to completion of the present invention. Further, the present inventors have found that the high filling content of the filler may be achieved by compounding the organic-inorganic composite filler of the present invention into the dental curable composition, and as a result, it may be possible that the dental curable composition has a high X-ray contrast property, an excellent surface luster after polishing, low polymerization shrinkage, high mechanical strength, and has excellent operability in which the past is hardly attached to a filling instrument due to little stickiness of the paste, leading to completion of the present invention.

Although the mechanism that the organic-inorganic composite filler of the present disclosure exhibits such excellent effects is unknown, it is thought that such excellent effects are exhibited by the following reason. In the preparation process of the organic-inorganic composite filler of the present disclosure, the silane compound is hydrolyzed by a trace amount of moisture contained in the polymerizable monomer or in the inorganic filler to generate —OH group. It is considered that the silane compound which generates the —OH group behaves as follows in the preparation process of the organic-inorganic composite filler of the present disclosure (1) a polymerizable monomer (a) having at least one functional group selected from the group consisting of —OH group, —NH— group and —NH$_2$ group forms a resin matrix in the organic-inorganic composite filler by copolymerizing with a polymerizable monomer (b) having no functional group selected from the group consisting of —OH group, —NH— group, and —NH$_2$ group. These functional groups contained in the resin matrix interacts with —OH group generated by hydrolysis of the silane compound to generate covalent bonding or hydrogen bonding, and thereby —OH group of the silane compound is introduced. When an organic group (not having a polymerizable group) is present in the silane compound, the wettability with respect to the resin matrix is improved and cohesiveness inside the resin matrix is improved. On the other hand, when the organic group of the silane compound includes a polymerizable group, the silane compound is copolymerized at the same time as forming the resin matrix by copolymerizing the polymerizable monomer (a) and the polymerizable monomer (b), to be incorporated into the resin matrix, and the —OH group is introduced.

(2) A plurality of silane compounds are hydrolyzed and condensed to form a low condensate having a siloxane network, and the siloxane network is complexly intertwined with the resin matrix.

(3) Superfine particle silica particles are prepared by three-dimensional hydrolysis and condensation of the silane compounds, and the superfine particle silica particles are uniformly dispersed in the resin matrix (4) The silane compound reacts with the surface of the inorganic filler by covalent bonding or hydrogen bonding generated by interacts the silanol group on the surface of the inorganic filler and —OH group generated by hydrolysis of the silane compound. When the silane compound does not have an organic group, the remaining —OH group of the silane compound reacted with the inorganic filler also reacts with a specific functional group in the resin matrix to act as a binder for bonding the inorganic filler and the resin matrix. In addition, when the silane compound has an organic group (not having a polymerizable group), the inorganic filler may be hydrophobized to improving the wettability with respect to the resin matrix and therefore dispersibility and cohesiveness are further improved. Further, when the organic group of the silane compound has a polymerizable group, the silane compound which reacts with the inorganic filler is copolymerized at the same time as forming the resin matrix by copolymerizing the polymerizable monomer (a) and the polymerizable monomer (b). Therefore, the inorganic filler may be bonded to the side chain of the resin matrix.

It is considered that the behaviors of the above (1) to (4) are complexly exhibited in preparation of the organic-inorganic composite filler of the present disclosure using a polymerizable monomer having a specific functional group, a polymerizable monomer not having a specific functional group, an inorganic filler, a polymerization initiator, and a silane compound which generates an —OH group by hydrolysis. As a result, the mechanical properties of the organic-inorganic composite filler of the present disclosure are remarkably improved as compared with the conventional organic-inorganic composite filler. Also, since many OH groups due to the silane compound are present in the resin matrix in the organic-inorganic composite filler of the present disclosure, it may be possible that the organic-inorganic composite filler of the present disclosure may be uniformly surface-treated with a silane coupling agent to highly hydrophobize the organic-inorganic composite filler. Therefore, the dental curable composition compounded with the organic-inorganic composite filler of the present disclosure exhibits the effect of the present disclosure.

The present inventor(s) of the present disclosure provides the following disclosure in the present application.

Specifically, provided is an organic-inorganic composite filler containing a polymerizable monomer (a) having at least one functional group selected from the group consisting of —OH group, —NH— group, and —NH$_2$ group, a polymerizable monomer (b) having no functional group selected from the group consisting of —OH group, —NH— group, and —NH$_2$ group, a polymerization initiator (c), an inorganic filler (d), and a silane compound (e) which generates —OH group by hydrolysis and is represented by the following formula (1).

[Formula 1]

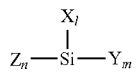

(1)

(wherein X represents halogen or —NCO, Y represents —OR (R represents H or alkyl group having 1 to 4 carbon atoms), Z represents saturated hydrocarbon group and/or an unsaturated hydrocarbon group arbitrarily containing hetero atom and having 1 to 20 carbon atoms, $l+m+n=4$, $l=0$ to 3, $m=1$ to 4, and $n=0$ to 3 are satisfied)

Advantageous Effects of Invention

The present invention provides a dental curable composition having a high X-ray contrast property, an excellent surface luster after polishing, high transparency, low polymerization shrinkage and high mechanical strength, and further having little stickiness of the paste and excellent operability by compounding the organic-inorganic composite filler of the present invention in the dental curable composition.

DETAILED DESCRIPTION OF THE PREFERRED EMBODIMENTS

Hereinafter, each component of an organic-inorganic composite filler of the present disclosure and a dental curable composition containing the organic-inorganic composite filler will be described in detail below.

A polymerizable monomer (a) having at least one functional group selected from the group consisting of —OH group, —NH— group, and —NH$_2$ group which may be used for preparing the organic-inorganic composite filler of the present disclosure may form a resin matrix in the organic-inorganic composite filler by copolymerizing with a polymerizable monomer (b) having no functional group selected from the group consisting of —OH group, —NH— group, and —NH$_2$ group.

As the polymerizable monomer (a), any of known monofunctional and/or polyfunctional polymerizable monomers commonly used in the dental field may be suitably used without any limitation, as far as the polymerizable monomer has at least one functional group selected from the group consisting of —OH group, —NH— group, and —NH$_2$ group. Representative examples include a polymerizable monomer having an acryloyl group and/or a methacryloyl group. In the present disclosure, the term "(meth)acrylate" or "(meth)acryloyl" inclusively refers to both of an acryloyl group-containing polymerizable monomer and a methacryloyl group-containing polymerizable monomer.

Specific examples of the polymerizable monomer (a) having —OH group include 2,2-bis[4-(3-methacryloyloxy-2-hydroxypropoxy) phenyl] propane, 2-hydroxy-3-acryloyloxypropyldi(meth)acrylate.

Specific examples of the polymerizable monomer (a) having —NH— group include di (meth) acrylate, etc., having a bifunctional, or a trifunctional or a higher functional urethane bond and derived from an adduct of a polymerizable monomer having a hydroxyl group such as 2-hydroxyethyl (meth) acrylate, 2-hydroxypropyl (meth) acrylate, or 3-chloro-2-hydroxypropyl (meth) acrylate, and a diisocyanate compound such as methylcyclohexanediisocyanate, methylenebis (4-cyclohexyl isocyanate), hexamethylenediisocyanate, trimethylhexamethylenediisocyanate, isophoronediisocyanate, diisocyanatemethylmethylbenzene, or 4,4-diphenylmethanediisocyanate.

Specific examples of the polymerizable monomer (a) having —NH$_2$ group include p-vinyl aniline, aminomethyl (meth) acrylate, aminoethyl (meth) acrylate, and aminopropyl (meth) acrylate. The polymerizable monomer (a) may contain a plurality of these same functional groups or of different functional groups in one molecule without any limitation.

Further, the polymerizable monomer (a) can be used not only singly but also in combinations of two or more. In the present disclosure, because it is necessary that the refractive index after curing of the resin matrix comprising the polymerizable monomer (a), the polymerizable monomer (b) and the polymerization initiator (c) is approximated to the refractive index of the inorganic filler (d), it is preferable that the polymerizable monomer (a) and the polymerizable monomer (b) are combined with plural types of polymerizable monomers to control the refractive index of the resin matrix. In addition to the above described polymerizable monomer (a), a polymerizable monomer having an acidic group such as a phosphate group, a phosphonate group, a carboxylic acid group, and a sulfonate group, a polymerizable monomer having a sulfur atom in molecule, a polymerizable monomer having a fluoro group, a polymerizable monomer having halogen or an organic group, a (meth) acrylamide derivative, and, a monomer, an oligomer and a polymer which have the above described specific functional group (—OH group, —NH— group, —NH$_2$ group) and at least one or more polymerizable group.

A polymerizable monomer (b) having no functional group selected from the group consisting of —OH group, —NH— group, and —NH$_2$ group which may be used for preparing the organic-inorganic composite filler of the present disclosure may form a resin matrix in the organic-inorganic composite filler by copolymerizing with a polymerizable monomer (a) polymerizable monomer (a) having at least one functional group selected from the group consisting of —OH group, —NH— group, and —NH$_2$ group. As the polymerizable monomer (b), any of known monofunctional and/or polyfunctional polymerizable monomers commonly used in the dental field may be suitably used without any limitation, as far as the polymerizable monomer has no functional group selected from the group consisting of —OH group, —NH— group, and —NH$_2$ group. Representative examples include a polymerizable monomer having an acryloyl group and/or a methacryloyl group. In the present disclosure, the term "(meth)acrylate" or "(meth)acryloyl" inclusively refers to both of an acryloyl group-containing polymerizable monomer and a methacryloyl group-containing polymerizable monomer. Any of known monofunctional and/or polyfunctional polymerizable monomers commonly used in the dental curable composition may be suitably used without any limitation.

Specific examples of the polymerizable monomers are as follows.

(I) Mono-Functional Polymerizable Monomer:
Methyl (meth) acrylate, ethyl (meth) acrylate, butyl (meth) acrylate, hexyl (meth) acrylate, glycidyl (meth) acrylate, lauryl (meth) acrylate, cyclohexyl (meth) acrylate, allyl (meth) acrylate, 2-ethoxyethyl (meth) acrylate, methoxypolyethyleneglycol (meth) acrylate, glycerin (meth) acrylate, isopropyl (meth) acrylate, isobutyl (meth) acrylate, 2-ethylhexyl (meth) acrylate, tetrahydrofurfuryl (meth) acrylate, benzyl (meth) acrylate, isobornyl (meth) acrylate, etc.

(II) Aromatic Bifunctional Polymerizable Monomer:
2,2-bis (4-(meth) acryloyloxyphenyl) propane, 2,2-bis (4-(meth) acryloyloxyethoxyphenyl) propane, 2,2-bis (4-(meth) acryloyloxy diethoxyphenyl) propane, 2,2-bis (4-(meth) acryloyloxy tetraethoxyphenyl) propane, 2,2-bis (4-(meth) acryloyloxy pentaethoxyphenyl) propane, 2,2-bis (4-(meth) acryloyloxy dipropoxyphenyl) propane, 2(4-(meth) acryloyloxy ethoxyphenyl)-2(4-(meth) acryloyloxy diethoxyphenyl) propane, 2(4-(meth) acryloyloxy diethoxyphenyl)-2(4-(meth) acryloyloxy triethoxyphenyl) propane, 2(4-(meth) acryloyloxy dipropoxyphenyl)-2(4-(meth) acryloyloxy triethoxyphenyl) propane, 2,2-bis (4-(meth) acryloyloxy dipropoxyphenyl) propane, 2,2-bis (4-(meth) acryloyloxy isopropoxyphenyl) propane, 2,2-bis (4-(meth) acryloyloxy polyethoxyphenyl) propane, etc.

(III) Aliphatic Bifunctional Polymerizable Monomer:
Ethyleneglycoldi (meth) acrylate, diethyleneglycoldi (meth) acrylate, triethyleneglycoldi (meth) acrylate, butyleneglycoldi (meth) acrylate, polyethyleneglycoldi (meth) acrylate, neopentylglycoldi (meth) acrylate, propyleneglycoldi (meth) acrylate, tricyclodecanedi (meth) acrylate, 1,3-butanedioldi (meth) acrylate, 1,4-butanedioldi (meth) acrylate, glycerindi (meth) acrylate, 1,6-hexanedioldi (meth) acrylate, 1,9-nonanedioldi (meth) acrylate, hydroxy pivalic acid-neopentylglycoldi (meth) acrylate, etc.

(IV) Trifunctional Polymerizable Monomer:
Trimethylolpropanetri (meth) acrylate, trimethylolethanetri (meth) acrylate, trimethylolmethanetri (meth) acrylate, pentaerythritoltri (meth) acrylate, etc.

(V) Tetrafunctional Polymerizable Monomer:
Pentaerythritoltetra (meth) acrylate, ditrimethylolpropanetetra (meth) acrylate, etc.

The polymerizable monomer (b) can be used not only singly but also in combinations of two or more. In the present disclosure, because it is necessary that the refractive index after curing of the resin matrix comprising the polymerizable monomer (a), the polymerizable monomer (b) and the polymerization initiator (c) is approximated to the refractive index of the inorganic filler (d), it is preferable that the polymerizable monomer (b) and the polymerizable monomer (a) are combined with plural types of polymerizable monomers to control the refractive index of the resin matrix. In addition to the above described polymerizable monomer (b), a polymerizable monomer having an acidic group such as a phosphate group, a phosphonate group, a carboxylic acid group, and a sulfonate group, a polymerizable monomer having a sulfur atom in molecule, a polymerizable monomer having a fluoro group, a polymerizable monomer having halogen or an organic group, a (meth)acrylamide derivative, and, a monomer, an oligomer and a polymer which do not have the above described specific functional group (—OH group, —NH— group, —NH$_2$ group) and at least one or more polymerizable group.

A polymerization initiator (c) which may be used for preparing the organic-inorganic composite filler of the present disclosure is not particularly limited, and any known polymerization initiator commonly used in the dental field such as a photo polymerization initiator, a chemical polymerization initiator, a thermal polymerization initiator may be used without any limitation.

As the thermal polymerization initiator, organic peroxides, azo compounds, and organometal compounds may be preferably used.

Specific examples of the organic peroxides include benzoyl peroxide, parachlorobenzoyl peroxide, 2,4-dichlorobenzoyl peroxide, acetyl peroxide, lauroyl peroxide, tert-butyl peroxide, cumenehydro peroxide, 2,5-dihydro peroxide, methylethylketone peroxide, and tert-butylperoxybenzoade.

Specific examples of the azo compounds include azobisisobutyronitrile, azobisisomethylisobutyrate, and azobiscyanovalerate.

Specific examples of the organometal compounds include organic boron compounds such as triphenylborane, tributylborane, and a partially oxidized tributylborane.

These thermal polymerization initiators can be used not only singly but also in combinations of two or more. In addition, these polymerization initiators have no problem even if subjected to a secondary treatment such as encapsulation in a microcapsule, if necessary.

As the chemical polymerization initiator, a redox type polymerization initiation system using the above described organic peroxides, such as an organic peroxide/an amine compound, an organic peroxide/an amine compound/a sulfonate, or an organic peroxide/an amine compound/a borate compound may be preferably used. Further, organometal compounds which initiate polymerization by reacting with oxygen or water, sulfinates and borate compounds which initiate polymerization by reacting with a polymerizable monomer having an acidic group, may be used.

Examples of the organic peroxides and the organometal compounds as the chemical polymerization initiator include the same as those used as the above described thermal polymerization initiator.

Preferably, specific examples of amine compounds are secondary or tertiary amine in which an amino group bonds to an aryl group, and specific examples thereof can be p-N,N-dimethyl-toluidine, N,N-dimethylaniline, N-β-hydroxyethyl-aniline, N, N-di(-hydroxyethyl)-aniline, p-N,N-di(β-hydroxyethyl)-toluidine, N-methyl-aniline, and p-N-methyl-toluidine.

Specific examples of sulfinates can be sodium benzenesulfinate, lithium benzenesulfinate, and sodium p-toluenesulfinate.

Specific examples of the borate compound can be sodium salts, lithium salts, potassium salts, magnesium salts, tetrabutylammonium salts, and tetramethylammonium salts of trialkylphenylboronate and trialkyl (p-phlorophenyl) borate (alkyl groups are an n-butyl group, an n-octyl group, an n-dodecyl group, etc.).

These chemical polymerization initiators can be used not only singly but also in combinations of two or more. In addition, these polymerization initiators have no problem even if subjected to a secondary treatment such as encapsulation in a microcapsule, if necessary.

On the other hand, for the photo polymerization initiator, photo sensitizers, and photo sensitizers/photo polymerization promotors or the like may be suitably used. Specific examples of the photo sensitizers may include α-diketones such as benzil, camphorquinone, α-naphtil, acetonaphtone, p,p'-dimethoxybenzil, p,p'-dichlorobenzylacetyl, pentadione, 1,2-phenanthrenquinone, 1,4-phenanthrenquinone, 3,4-phenanthrenquinone, 9,10-phenanthrenquinone and naphthoquinone; benzoin alkyl ethers such as benzoin, benzoin methyl ether and benzoin ethyl ether; thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone and 2,4-diisopropylthioxanthone; benzophenones such as benzophenone, p-chlorobenzophenone and p-methoxybenzophenone; acylphosphineoxides such as 2,4,6-trimethylbenzoyl diphenylphosphineoxide and bis (2,6-dimethoxybenzoyl)-2,4,4-trimethylpentylphosphineoxide; α-aminoacetophenones such as 2-benzyl-dimethylamino-1-(4-morpholinophenyl)-butanone-1,2-benzyl-diethyl-amino-1-(4-morpholinophenyl)propanone-1; ketals such as benzyldimethylketal, benzyldiethylketal and benzyl(2-methoxyethylketal); titanocenes such as bis (cyclopentadienyl)-bis[2,6-difluoro-3-(1-pyrolyl) phenyl] titanium, bis (cyclopentadienyl)-bis (pentanefluorophenyl) titanium and bis (cyclopentadienyl)-bis (2,3,5,6-tetrafluoro-4-disiloxyphenyl)-titanium.

Specific examples of the photo polymerization promotors may include tetriary amines such as N,N-dimethylaniline, N,N-diethylaniline, N,N-di-n-butylaniline, N,N-dibenzylaniline, p-N, N-dimethyl-toluidine, m-N, N-dimethyltoluidine, p-N,N-diethyltoluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoicacid ethyl ester, p-demtethylaminobenzoic acid amino ester, N,N-dimethylanthranilic acid methyl ester, N, N-dihydroxyethylaniline, p-N, N-dihydroxyethyl-toluidine, p-dimethylaminophenylalcohol, p-dimethylaminostyrene, N,N-dimethyl-3,5-xylidine, 4-dimethylaminopyridine, N, N-dimethyl-α-naphthylamie N,N-dimethyl-6-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate and 2,2'-(n-butylimino)diethanol; secondary amines such as N-phenylglycine; barbituric acids such as 5-butylbarbituric acid and 1-benzyl-5-phenylbarbituric acid; tin compounds such as dibutyltin diacetate, dibutyltin dilaurate, dioctyltin dilaurate, dioctyltin diperacetate, dioctyltin bis(mercaptoacetic acid isooctyl ester) salt and tetramethyl-1,3-diacetoxydistannoxane; aldehyde compounds such as laurylaldehyde and terephthalaldehyde; sulfur-containing compounds such as dodecylmercaptan, 2-mercaptobenzooxazole, 1-decanethiol and thiosalicylic acid.

In order to enhance photo polymerization promotion performance, it is effective to add, in addition to the above photo polymerization promoter, oxycarboxylic acids such as citric acid, malic acid, tartaric acid, glycolic acid, gluconic acid, α-oxyisobutyric acid, 2-hydroxypropanoic acid, 3-hydroxypropanoic acid, 3-hydroxybutanoic acid, 4-hydroxybutanoic acid and dimethylolpropionic acid.

These polymerization initiators may be used not only singly but also in combinations of two or more. In addition, these polymerization initiators have no problem even if subjected to a secondary treatment such as encapsulation in a microcapsule, if necessary.

Furthermore, these polymerization initiators can be used not only singly but also in combinations of two or more, regardless of the polymerization manner or the polymerization method.

Among these polymerization initiators, taking into account the use for the preparation of the organic-inorganic composite filler, a photo polymerization initiator and/or a thermal polymerization initiator may be preferably used because the timing of the polymerization may be optionally selected by giving an external energy such as light, and heat, and, the operation in preparation is simple. Furthermore, a thermal polymerization initiator is particularly preferable because the thermal polymerization initiator may be used without restriction in the work environment such as under the dark or under red light.

The content of the polymerization initiator (c) arbitrarily be selected from a range from 0.01 to 10 parts by weight for the whole amount of the polymerizable monomer (a) and the polymerizable monomer (b), more preferably in a range from 0.05 to 7 parts by weight, further preferably in a range from 0.1 to 5 parts by weight. When the content of the polymerization initiator (c) is less than 0.01 parts by weight, because the polymerizable monomer may be not polymerized and cured sufficiently in the preparation of the organic-inorganic composite filler, various effects including mechanical properties may be not obtained. Further, when the content of the polymerization initiator (c) exceeds 10 parts by weight, although the polymerizability and the curability may be not changed, discoloring is caused by remaining polymerization initiator.

An inorganic filler (d) which may be used for preparation of the organic-inorganic composite filler of the present disclosure is not particularly limited, and any known inorganic filler commonly used in the dental field may be used without any limitation.

Specific examples of the inorganic filler (d) include inorganic oxides such as silica, alumina, titania, zirconia, strontium oxide, barium oxide, yttrium oxide, lanthanum oxide, and ytterbium oxide, inorganic complex oxides such as silica-zirconia, silica-titania, silica-titania-barium oxide, and silica-titania-zirconia, glasses such as molten silica, quartz, borosilicate glass, aluminosilicate glass, borosilicate glass, alminoborate glass, and boroaluminosilicate glass, and, metallic fluorides such as calcium fluoride, barium fluoride, strontium fluoride, yttrium fluoride, lanthanum fluoride, and ytterbium fluoride.

These inorganic fillers may be used alone or in combination of two or more thereof. Among these, from a viewpoint of imparting a high X-ray contrast property to the dental curable composition compounded with the organic-inorganic composite filler, it is preferable that aluminosilicate glass, borosilicate glass, alminoborate glass, boroaluminosilicate glass or the like which include an inorganic oxide containing a heavy metal element such as strontium, barium, lanthanum and fluorine, or include the heavy metal element and fluorine, may be used as the inorganic filler used for preparation of the organic-inorganic composite filler. Further, a shape of the inorganic filler is not particularly limited, but arbitral particle shapes such as spherical, needle-like, plate-like, ground-like, scaly-shapes, and porous, and aggregate thereof may be used without any limitation.

An average particle diameter of the inorganic filler is not particularly limited, but in order to exhibit an excellent polishing property, and an excellent surface luster and glossiness after polishing of the dental curable composition containing the organic-inorganic composite filler of the present invention, the average particle diameter of the inorganic filler is preferably in the range from 0.01 to 3.0 µm, more preferably in the range from 0.1 to 2.0 µm, further preferably in the range from 0.1 to 1.0 µm, most preferably in the range from 0.1 to 0.4 µm. When then average particle diameter of the inorganic filler is less than 0.01 µm, since the specific surface area becomes large, the content of the inorganic filler in the organic-inorganic composite filler may be reduced. Therefore, the mechanical strength of the organic-inorganic composite filler may be reduced. When the average particle diameter of the inorganic filler exceeds 3.0 µm, the surface luster after polishing of the dental curable composition compounded with the organic-inorganic composite filler may decrease.

Further, in order to improve the wettability with respect to the polymerizable monomer in preparation of the organic-inorganic composite filler, it is preferable that these inorganic fillers is hydrophobized by surface treatment of the inorganic filler in advance. As the surface treatment agent used for the surface treatment of inorganic fillers, any known surface treatment agent such as organic silicon compounds, organic zirconium compounds, and organic titanium compounds, may be used without any limitation, and a silane coupling agent classified as an organic silicon compound is most commonly used in the dental field. Specific examples of the silane coupling agent include methyltrimethoxysilane, ethyltrimethoxysilane, methoxytripropylsilane, propyltriethoxysilane, hexyltrimethoxysilane, vinyltrimethoxysilane, vinyltriethoxysilane, vinyltrichlorosilane, vinyltri (β-methoxyethoxy) silane, γ-methacryloyloxypropyltrimethoxysilane, γ-glycidoxypropyltrimethoxysilane, γ-mercaptopropyltrimethoxysilane, γ-aminopropyltrimethoxysilane, 3-aminopropyltriethoxysilane, methyltrichlorosilane, phenyltrichlorosilane, trimethylsilylisocyanate, vinylsilyltriisocyanate, and phenylsilyltriisocyanate. Among these silane coupling agents, γ-methacryloyloxypropyltrimethoxysilane having excellent wettability with respect to the polymerizable monomer and polymerization performance is preferably used because of having the same polymerizable organic group as that of the polymerizable monomer contained in the organic-inorganic composite filler. These silane coupling agents may be used not only singly but also in combinations of two or more. The surface treatment method is not especially limited and any known method thereof is applicable. Further, the surface treatment quantity may arbitrarily be selected corresponding to the average particle diameter of the inorganic filler.

The content of the inorganic filler (d) used for preparation of the organic-inorganic composite filler may arbitrarily be selected in a range from 30 to 90 parts by weight, preferably is in a range from 50 to 90 parts by weight, more preferably is in a range from 60 to 90 parts by weight. When the content of the inorganic filler is less than 30 part by weight, an X-ray contrast property, hardness, and the mechanical strength of the organic-inorganic composite filler may decrease, therefore it may be difficult to obtain the effect of the present disclosure even if the organic-inorganic composite filler is compounded in the dental curable composition. Further, when the content of the inorganic filler exceeds 90 part by weight, it may be difficult that the inorganic filler is uniformly dispersed, therefore it may be difficult to stably prepare an organic-inorganic composite filler.

A silane compound (e) which may be used for preparing an organic-inorganic composite filler of the present disclosure is not particularly limited, and any known silane compound may be used without any limitation, as far as the silane compound is represented by the following formula (1).

[Formula 1]

(1)

(wherein X represents halogen or —NCO, Y represents —OR (R represents H or alkyl group having 1 to 4 carbon atoms), Z represents saturated hydrocarbon group and/or an unsaturated hydrocarbon group arbitrarily containing hetero atom and having 1 to 20 carbon atoms, 1+m+n=4, 1=0 to 3, m=1 to 4, and n=0 to 3 are satisfied)

Specific examples of the silane compound (e) include tetramethoxysilane, tetraethoxysilane, tetrapropylsilane, tetrabutoxysilane, methyltrimethoxysilane, ethyl trimethoxysilane, methoxytripropylsilane, propyltriethoxysilane, hexyltrimethoxysilane, vinyltrimethoxysilane, vinyltriethoxysilane, chlorotrimethoxysilane, vinyltri (β-methoxyethoxy) silane, γ-methacryloyloxypropyl trimethoxysilane, γ-glycidoxypropyltrimethoxysilane, γ-mercaptopropyl trimethoxysilane, γ-aminopropyltrimethoxysilane, β-aminopropyltriethoxysilane, trimethoxysilyl isocyanate, and triethoxysilyl isocyanate. Further, these silane compounds may be used not only singly but also in combinations of two or more. Furthermore, a silane condensation compound obtained by hydrolyzing and condensing these silane compounds in advance may be used.

Among these silane compounds, a silane compound having an organic group which may acts as a dispersing agent for improving the conformability between the polymerizable monomer and the inorganic filler in preparation of the organic-inorganic composite filler (n is 1 or more in the formula (1)) is preferably used. When the silane compound includes the organic group (not including a polymerizable group), because the inorganic filler may be hydrophobized, the wettability with respect to the resin matrix may be improved, and dispersibility and aggregability may be improved. Specific examples of the silane compound containing the organic group (not having a polymerizable group) include methyltrimethoxysilane, ethyltrimethoxysilane, methoxytripropylsilane, propyltriethoxysilane, hexyltrimethoxysilane, and γ-glycidoxypropyltrimethoxysilane.

Further, it is more preferable that the organic group of the silane compound has polymerizable group. When the organic group of the silane compound has polymerizable group, the silane compound which reacts with the inorganic filler is copolymerized at the same time as forming the resin matrix by copolymerizing the polymerizable monomer (a) and the polymerizable monomer (b). Therefore, the inorganic filler may be bonded to the side chain of the resin matrix. Specific examples of the silane compound having the organic group include vinyltrimethoxysilane, vinyltriethoxysilane, vinyltri (β-methoxyethoxy) silane, γ-methacryloyloxypropyl trimethoxysilane. Among them, γ-methacryloyloxypropyl trimethoxysilane is more preferably used.

The content of the silane compound (e) used for preparation of the organic-inorganic composite filler may arbitrarily be selected, and preferably is in a range from 1 to 50 parts by weight, and more preferably is in a range from 1 to 30 parts by weight. When the content of the silane compound in preparation of the organic-inorganic composite filler is less than 1 part by weight, it is difficult to exhibit the effect of compounding a silane compound, and it is difficult to impart the effects of the present disclosure to the organic-inorganic composite fillers. On the other hand, when the content of the silane compound exceeds 50 part by weight, there is a possibility that the hardness and mechanical strength of the organic-inorganic composite filler is adversely affected.

The preferable organic-inorganic composite filler of the present disclosure are also characterized by having excellent transparency. This feature may be achieved by approximating the refractive index after curing of the resin matrix containing the polymerizable monomer (a), the polymerizable monomer (b), and the polymerization initiator (c), and the refractive index of the inorganic filler. Specifically, it is necessary that the relationship between the refractive index "nR" after curing of the resin matrix containing the polymerizable monomer (a), the polymerizable monomer (b), and the polymerization initiator (c) and the refractive index "nD" of the inorganic filler satisfies the following formula (2).

[Formula 2]

$$0 \le |nR - nD| < 0.03 \quad (2)$$

When the difference between the refractive index "nR" after curing of the resin matrix and the refractive index "nD" of the inorganic filler exceeds 0.03, the difference in refractive index between the resin matrix after curing and the inorganic filler is large, therefore turbidity generates in the organic-inorganic composite filler. Therefore, it is difficult to adjust the transparency even in the dental curable composition compounded with the organic-inorganic composite filler. As a result, it is impossible to impart high transparency to the dental curable composition compounded with the organic-inorganic composite filler unless the other properties are sacrificed.

In preparing step of the organic-inorganic composite filler of the present disclosure, the kind and mixing ratio of the polymerizable monomer used for the polymerizable monomer (a) and/or the polymerizable monomer (b), is adjusted. Thereby, the refractive index of the resin matrix obtained by polymerizing and curing the mixture of these polymerizable monomer may be approximated to the refractive index of the inorganic filler to impart high transparency to the organic-inorganic composite filler of the present disclosure. Further, the polymerization initiator is also a constituent of the resin matrix, and give not a little influence on the refractive index. However, because the content is small, the influence on the refractive index is considered to be small. However, if the content is large, the refractive index is affected. Therefore, it is necessary to adjust the mixing ratio or the like with respect to polymerization initiator as well as the polymerizable monomer.

The preparation method of the organic-inorganic composite filler is not especially limited and any method thereof may be employed, and the preparation method is preferably a preparation method of the organic-inorganic composite filler using a thermal polymerization initiator as a polymerization initiator, which method has been performed in the dental field conventionally. Although the preparation method of the organic-inorganic composite filler which has been performed in the dental field conventionally is described herein, the effects of the present disclosure is also described.

In conventional method, firstly, the polymerizable monomer, the polymerization initiator, and the inorganic filler are mechanically kneaded using a mortar, a kneader, a roll, a raikai mixer etc., to prepare a uniform paste. In another embodiment, the polymerizable monomer and the polymerization initiator are mixed to prepare a resin mixture in advance, and then the resin mixture and the inorganic filler are mechanically kneaded to prepare a paste. At this time, in order to increase the content of the inorganic filler in the paste, it is necessary to increase the wettability with respect to the resin component which is the polymerizable monomer by surface treatment of the surface of the inorganic filler with a silane coupling agent in advance. Therefore, it is necessary that the inorganic filler is surface treated with the silane coupling agent in advance in the preceding process.

In preparation of the organic-inorganic composite filler of the present disclosure, a resin mixture containing a polymerizable monomer, a polymerization initiator, and a silane compound, and an inorganic filler which is not surface treated with the silane coupling agent in advance, are mixed (integral blend). Therefore, the inorganic filler may be uniformly dispersed in the resin mixture, and it is possible to prepare a paste highly filled with the inorganic filler. The filler content of the inorganic filler in the paste is increased by this method as compared with the case that the inorganic filler is surface treated with a silane coupling agent in advance. Moreover, this preparation method may simplify the manufacturing steps because of omitting the step of the surface treatment of the inorganic filler with a silane coupling agent in advance. Therefore, it is one advantage of the present disclosure that preparation cost may be suppressed.

The paste may be caused to polymerize using proper polymerization equipment such as a hot press. The polymerization temperature only has to properly be selected corresponding to the decomposition temperature of the polymerization initiator while, preferably, the polymerization temperature is in a range from 20 to 250° C. and, more preferably, is in a range from 60 to 200° C. The polymerization time period only has to properly be selected taking into consideration the polymerization state of the polymerized substance and the amount of remaining unreacted monomers. The polymerization can also generally be caused to take place in an inert gas such as nitrogen or argon to prevent any change of the color of the polymerized substance. Polymerization under the atmospheric pressure is sufficient as the polymerization while the polymerization can also be caused to take place under an increased pressure as necessary. The preparation and the polymerization of the paste can also be caused to concurrently take place using a kneader such as a pressurizing kneader.

After the polymerization of the paste, the polymerized substance is crushed to acquire an organic-inorganic composite filler. The crushing method is not especially limited while the crushing can be executed in a method generally employed in the dental field. For example, the method can be a method using a container driven medium mill such as a ball mill or a vibration mill, a high speed rotation mill such as a hammer mill or a turbo mill, or a medium agitation mill such as a sand grinder or an attritor, and can properly be selected corresponding to the necessary average particle diameter. The crushing can also be executed in an atmosphere of an inert gas or a solvent such as alcohol to prevent any coloring of the crushed substance during the crushing. The crushing can also be executed with an antioxidizing agent such as, for example, a known phenol such as hydroquinone monomethyl ether added to the polymerized paste. Preferably, the average particle diameter of the crushed organic-inorganic composite filler is in a range from 1 to 100 μm. More preferably, the average particle diameter thereof is in a range from 3 to 50 μm and, yet more preferably, is in a range from 5 to 30 μm.

It is preferable that the organic-inorganic composite filler of the present disclosure is surface treated with abovementioned silane coupling agent after grinding, and then compounded in the dental curable composition. Since the organic-inorganic composite filler of the present disclosure has many reaction sites to a silane coupling agent on the surface, the surface of the organic-inorganic composite filler is highly hydrophobized by surface treatment using a silane coupling agent. As a result, it is possible to highly fill the organic-inorganic composite filler in the dental curable composition, and the effect of improving mechanical strength and the effect of reducing polymerization shrinkage may be exhibited. Silane coupling agent used for the surface treatment of the organic-inorganic composite filler may be the same kind of the silane coupling agent which is used for the surface treatment of the inorganic filler in order to improve the conformability between the inorganic filler and the polymerizable monomer in the preparation of the organic-inorganic composite filler. Specific examples of the silane coupling agent include methyltrimethoxysilane, ethyltrimethoxysilane, methoxytripropylsilane, propyltriethoxysilane, hexyltrimethoxysilane, vinyltrimethoxysilane, vinyltriethoxysilane, vinyltrichlorosilane, vinyltri (6-methoxyethoxy) silane, γ-methacryloyloxypropyltrimethoxysilane, γ-glycidoxypropyltrimethoxysilane, γ-mercaptopropyltrimethoxysilane, γ-aminopropyltrimethoxysilane, 3-aminopropyltriethoxysilane, methyltrichlorosilane, phenyltrichlorosilane, trimethylsilylisocyanate, vinylsilyltriisocyanate, and phenylsilyltriisocyanate.

Among these silane coupling agents, γ-methacryloyloxypropyltrimethoxysilane having excellent wettability with respect to the polymerizable monomer and polymerization performance is preferably used because of having the same polymerizable organic group as that of the polymerizable monomer contained in the dental curable composition. These silane coupling agents may be used not only singly but also in combinations of two or more. The surface treatment method is not especially limited and any known method thereof is applicable. Further, the surface treatment quantity may arbitrarily be selected corresponding to the average particle diameter of the inorganic filler.

The organic-inorganic composite filler of the present disclosure may be highly hydrophobized by surface treatment using a silane coupling agent, and the degree of hydrophobicity may be measured by the contact angle. The contact angle of the organic-inorganic composite filler of the present disclosure is preferably 100° or more, more preferably 105° or more, further preferably 110° or more. When the contact angle is less than 100°, wettability of the dental curable composition compounded with the organic-inorganic composite filler with respect to the resin component which is the polymerizable monomer, therefore, it may be not possible to highly fill the organic-inorganic composite filler in the dental curable composition.

In another method for measuring the degree of hydrophobicity of the organic-inorganic composite filler, the degree of hydrophobicity may be determined by the method described in item <Consistency> in Example. When the consistency of the paste is high, wettability of the organic-inorganic composite filler with respect to the resin component which is the polymerizable monomer is improved, therefore, it may be possible to highly fill the organic-inorganic composite filler in the paste.

The content of the organic-inorganic composite filler in the dental curable composition is preferably in a range from 5 to 80 parts by weight, more preferably in a range from 10 to 75 parts by weight, further preferably in a range from 15 to 70 parts by weight. When the content of the organic-inorganic composite filler in the dental curable composition is less than 5 parts by weight, the adhesiveness of the paste becomes high and polymerization shrinkage becomes large. Therefore it is not preferable. Further, when the content of the organic-inorganic composite filler in the dental curable composition exceeds 80 parts by weight, the roughness of paste increases to deduce the smoothness of the paste and it may be difficult to spread the paste with a spatula or the like. Therefore it is not preferable.

A polymerizable monomer (g) which may be contained in the dental curable composition of the present disclosure is not particularly limited, and any known polymerizable monomer commonly used in the dental field. Among them, it is preferable to use at least one polymerizable monomer which is the same as the polymerizable monomer (a) having the specific functional group or the polymerizable monomer (b) not having the specific functional group which are used for aforementioned preparation of the organic-inorganic composite filler of the present disclosure. It is more preferable to use the same kind of polymerizable monomer as the polymerizable monomer (a) and the polymerizable monomer (b). Thus, compatibility between the organic-inorganic composite filler of the present disclosure and the resin component which is the polymerizable monomer is improved, therefore it is possible to achieve a high filling content of the filler in the dental curable composition.

An inorganic filler (h) which may be contained in the dental curable composition of the present disclosure is not particularly limited, and any known inorganic filler commonly used in the dental field. Among them, it is preferable to use an inorganic filler having the same average particle diameter and the same shape as the inorganic filler (d) used for preparation of the organic-inorganic composite filler. The content of the inorganic filler (h) in the dental curable composition is preferably in a range from 5 to 80 parts by weight, more preferably in a range from 10 to 75 parts by weight, further preferably in a range from 15 to 70 parts by weight. When the content of the inorganic filler in the dental curable composition is less than 5 parts by weight, the mechanical strength of the dental curable composition may be decrease. Further, when the content of the inorganic filler in the dental curable composition exceeds 80 parts by weight, it may be difficult that the inorganic filler is uniformly dispersed, therefore it may be difficult to stably prepare a dental curable composition.

The dental curable composition of the present invention may be imparted with high mechanical strength, low polymerization shrinkage, an excellent surface luster and glossiness after polishing, and paste properties in which the past is hardly attached to a filling instrument and has excellent formability, by highly filling the combination of the organic-inorganic composite filler (f) and the inorganic filler (h) in the dental curable composition.

The total content of the organic-inorganic composite filler (f) and the inorganic filler (h) in the dental curable composition is preferably 60 parts by weight or more, more preferably 70 parts by weight or more, further preferably 80 parts by weight or more. When the total content of the organic-inorganic composite filler (f) and the inorganic filler (h) in the dental curable composition is less than 60 parts by weight, because the adhesiveness of the paste may be high, paste property may have poor formability, and further polymerization shrinkage may become large.

A polymerization initiator (i) which may be contained in the dental curable composition of the present disclosure is not particularly limited, and any known polymerization initiator commonly used in the dental field, and may be suitably selected from among the above described polymerization initiators (c) used in the preparation of the organic-inorganic composite filler of the present disclosure, and may be used.

Among these polymerization initiators, a preferred aspect is use of the photo polymerization initiator, which generates radicals when a light beam is applied thereto and that is most advantageously used based on the fact that the photo polymerization initiator can cause the dental curable composition to polymerize when little air is included in the dental curable composition. The photo polymerization initiator is preferably a combination of an α-diketone and a tertiary amine and more preferably, a combination of camphorquinone with an aromatic amine having an amino group directly bound to the benzene ring such as ethyl p-N,N-dimethylaminobenzoate or with an aliphatic amine having a double bond in the molecule such as N,N-dimethylaminoethyl methacrylate. In embodiments, depending upon the use, a sensitizing pigment such as coumalin, cyanine, and thiazine; a light acid generator which produces Broensted acid or Lewis acid by light irradiation such as a s-triazine derivative substituted with a halomethyl group or diphenyl iodonium salt compound; quaternary ammonium halides; and transition metal compound may be used.

The content of the polymerization initiator (i) contained in the dental curable composition of the present disclosure may arbitrarily be selected corresponding to the use while, preferably, the content thereof is in a range from 0.01 to 10 parts by weight for the whole amount of the polymerizable monomer (g), more preferably is in a range from 0.05 to 7 parts by weight, further preferably is in a range from 0.1 to 5 parts by weight. When the content of polymerization initiator (i) is less than 0.01 part by weight, it is difficult to obtain the effect of the polymerization initiator. Further, when the content of polymerization initiator (i) exceeds 10 part by weight, there is a risk that the polymerization initiator is liquated from the cured product.

In addition to the (a) to (i) components, known additives may be compounded in the dental curable composition of the present disclosure each within a range not to degrade the effect of the present disclosure. For example, the additives can be fillers other than (f) the organic-inorganic composite filler and other than (d) the inorganic filler, polymerization-inhibitors, antioxidizing materials, ultraviolet absorbing materials, antibacterial materials, dyes, and pigments.

The dental curable composition of the present disclosure may be prepared by mixing the above components.

The packaging form of the dental curable composition of the present disclosure is not especially limited, and any one of a one-pack packaging form, two-pack packaging form, and another form may be used depending on the type of the polymeric initiator or the purpose of use. The packaging form can arbitrarily be selected corresponding to the use.

EXAMPLES

The present disclosure is described in more detail and specifically with reference to Examples. However, the present disclosure is not limited to Examples.

The materials used in Examples and Comparative Examples and their abbreviations are listed below.

[Polymerizable monomer (a): the polymerizable monomer having at least one functional group selected from the group consisting of —OH group, —NH— group, and —NH$_2$ group.]
Bis-GMA: 2,2-bis [4-(3-methacryloyloxy-2-hydroxypropoxy) phenyl] propane (the refractive index before curing: 1.55)
UDMA: N,N-(2,2,4-trimethylhexamethylene) bis [2-(aminocarboxy) ethanol]methacrylate (the refractive index before curing: 1.48)
[Polymerizable monomer (b): the polymerizable monomer having no functional group selected from the group consisting of —OH group, —NH— group, and —NH$_2$ group.]
Bis-MPEPP: 2,2-bis (4-methacryloyloxy polyethoxyphenyl) propane (the refractive index before curing: 1.54)
3G: Triethyleneglycol dimethacrylate (the refractive index before curing: 1.46)
[Inorganic Filler]
Inorganic filler A: Fluoroaluminosilicate glass filler (the average particle diameter: 0.4 μm, the refractive index nD: 1.53)
Inorganic filler B: Fluoroaluminosilicate glass filler (the average particle diameter: 0.4 μm, the refractive index nD: 1.53), and the surface of 100 parts by weight was subjected to surface treatment with 9 parts by weight of MPS in accordance with an ordinary method.
Inorganic filler C: Fluoroaluminosilicate glass filler (the average particle diameter: 1 μm, the refractive index nD: 1.53) and the surface of 100 parts by weight was subjected to surface treatment with 6 parts by weight of MPS in accordance with an ordinary method.

Aerosil R711 (an ultra fine particle filler)
[Silane Compound]
TEOS: tetraethoxysilane
MEOS: methyl triethoxysilane
MPS: γ-methacryloyloxypropyltrimethoxysilane
[Polymerization Initiator]
DMABE: N,N-dimethylamino ethylbenzoate
BPO: Benzoyl peroxide
CQ: α-camphorquinone
[Silane Coupling Agent]
MPS: γ-methacryloyloxypropyltrimethoxysilane The testing methods employed for Examples and Comparative Examples are as follows.

(1) Contact Angle

In the method of measuring the contact angle, a surface-treated organic-inorganic composite filler is molded by pressing for 1 minute under a load of 20 tf to prepare a powder block. The contact angle was measured on the surface of the powder block after 10 seconds from immediately after dropping 5.0 cc of water.

(2) Transparency

A uniform paste was prepared by mixing 72.5 parts by weight of a surface-treated organic-inorganic composite filler, 2.5 parts by weight of Aerosil R711, and 25 parts by weight of a liquid mixture resin which is used for confirmation of transparency and then uniformly kneading. The liquid mixture resin which is used for confirmation of transparency was a mixture consisting of 100 parts by weight of a mix polymerizable monomer prepared by mixing the polymerizable monomer (a) and the polymerizable monomer (b) in the same ratio as the preparation of the organic-inorganic composite filler, which are used for preparing the organic-inorganic composite filler, 1 parts by weight of DMABE, and 0.3 part by weight of CQ. Then, a stainless steel mold (the inner diameter: 15 mm, the thickness: 1 mm) was filled with the paste and cover glasses were placed on both sides to press.

Thereafter, a light beam was applied from the side faces each for three min using a visible light curing unit (Solidilite V: manufactured by Shofu Inc.) and, thereby, a cured body was obtained. The cured body was placed on a paper in which characters are printed, and transparency was visually determined. The rating criteria were as follow.
A: The character in the background was clearly determined and transparency was especially excellent.
B: The character in the background was easily determined and transparency was excellent.
C: The character in the background was not easily determined and transparency was inferior.

(3) Bending Strength

The dental curable composition was filled into a stainless steel mold, and the cover glasses are placed on both sides to press with a glass kneading plate. Thereafter, light is irradiated for 10 seconds to 5 locations by using the light curing unit (Blue Shot manufactured SHOFU Inc.) to curing the dental curable composition. After curing, the cured product was removed from the mold, and light is irradiated to the backside in the same manner again to use as a measurement specimen (25×2×2 mm rectangular shape). The specimen was immersed in water at 37° C. for 24 hours, and thereafter bending test was performed.

Bending test was performed using an Instron universal tester (Instron 5567 manufactured by Instron) at a distance between supporting points of 20 mm and a crosshead speed of 1 mm/min. The number of the specimen is 10 and the bending strength is evaluated by the average.

(4) Consistency

The dental curable composition was statically stored in a temperature-controlled chamber at 25° C. (the humidity: 50%) for one day, and 300 mm³ of the dental curable composition was weighed on a glass plate. Another glass plate was put on the dental curable composition and a weight weighing 385 g was further placed thereon. Thereafter, the dental curable composition was left in this state for three min. After three min, the weight was removed, and the dimensions between parallel cutting lines of the dental curable composition spread in a circle were measured at two points. The average value of the values at the two points was taken as the initial consistency (mm).

(5) Polymerization Volume Shrinkage

A stainless steel mold (the inner diameter: 10 mm, the thickness: 2 mm) was filled with the dental curable composition and cover glasses were placed on its both side faces to be brought into pressurized contact with the mold. Thereafter, a light beam was applied to the dental curable composition from the side faces each for three min using a visible light curing unit (Solidilite V: manufactured by Shofu Inc.) and, thereby, a cured body of the dental curable composition was obtained. The densities of the dental curable composition before and after light-curing were measured using a gas pycnometer (Acupyc 1303: manufactured by Micromeritics), and the polymerization volume shrinkage was calculated from the acquired measurements according to formula (3). The measurement of the densities was conducted at 25° C.

[Formula 3]

$$\text{Polymerization volume shrinkage (vol \%)} = (1 - D_{before}/D_{after}) \times 100 \quad (3)$$

($D_{before}$: The density of the dental curable composition before light-curing, $D_{after}$: The density of the dental curable composition after light-curing)

(6) Operability

The operability of the paste was evaluated by filling the dental curable composition into a model of class I cavity under 37° C. and 100% humidity environment. The rating criteria of the operability at the time of filling the composition were as follow.
A: Less sticky feeling and less dry feeling were exhibited, and filling operability was particularly excellent.
B: Less sticky feeling and less dry feeling were exhibited, and filling operation was easy.
C: Strong sticky feeling and strong dry feeling were exhibited, and operation was difficult.

(7) Surface Glossiness

The surface of the cured body of the dental curable composition was polished with waterproof abrasive paper #320, and was finish polished with Compo Master (manufactured by Shofu Inc.) for 30 seconds. The glossiness of the surface was visually determined. The rating criteria were as follow.
A: Surface glossiness was particularly excellent.
B: Surface glossiness was excellent.
C: Surface glossiness was inferior.

In accordance with the following procedure, the organic-inorganic composite fillers A to P shown in Table 1 were prepared. Further, the contact angle, the relationship between a refractive index after curing the resin matrix cure: nR and a refractive index of the inorganic filler (d): nD, and the determination result of the transparency with respect to the organic-inorganic composite filler A to P are shown in Table 2.

[Preparation of Organic-Inorganic Composite Filler A]

A uniform paste was prepared by mixing 25 parts by weight of a liquid resin, 2.5 parts by weight of Aerosil R711, and 72.5 parts by weight of the inorganic filler B and then uniformly kneading. The liquid resin was a mixture consisting of 47 parts by weight of Bis-GMA, 47 parts by weight of 3G, 6 parts by weight of TEOS, and 0.5 part by weight of BPO. The paste was cured by heating for 4 hours at 100° C. under a nitrogen atmosphere, and grinded and classified to obtain a powder having 25 μm average particle diameter. Further, surface treatment was performed for 100 parts by weight of the powder with 6 parts by weight of MPS in accordance with an ordinary method to obtain an organic-inorganic composite filler A. This organic-inorganic composite filler A was excellent in transparency and was measured for the contact angle. The result was 112°.

[Preparation of Organic-Inorganic Composite Filler B]

An organic-inorganic composite filler B was obtained by the same manner as in the organic-inorganic composite filler A. However, the inorganic filler A was used instead of the inorganic filler B. This organic-inorganic composite filler B was excellent in transparency and was measured for the contact angle. The result was 118°.

[Preparation of organic-inorganic composite filler C]

An organic-inorganic composite filler C was obtained by the same manner as in the organic-inorganic composite filler A. However, MEOS was used instead of TEOS. This organic-inorganic composite filler C was excellent in transparency and was measured for the contact angle. The result was 115°.

[Preparation of Organic-Inorganic Composite Filler D]

An organic-inorganic composite filler D was obtained by the same manner as in the organic-inorganic composite filler C. However, the inorganic filler A was used instead of the inorganic filler B. This organic-inorganic composite filler D was excellent in transparency and was measured for the contact angle. The result was 114°.

[Preparation of Organic-Inorganic Composite Filler E]

An organic-inorganic composite filler E was obtained by the same manner as in the organic-inorganic composite filler A. However, MPS was used instead of TEOS. This organic-inorganic composite filler E was excellent in transparency and was measured for the contact angle. The result was 118°.

[Preparation of Organic-Inorganic Composite Filler F]

An organic-inorganic composite filler F was obtained by the same manner as in the organic-inorganic composite filler E. However, the inorganic filler A was used instead of the inorganic filler B. This organic-inorganic composite filler F was excellent in transparency and was measured for the contact angle. The result was 117°.

[Preparation of Organic-Inorganic Composite Filler G]

An organic-inorganic composite filler G was obtained by the same manner as in the organic-inorganic composite filler A. However, the inorganic filler C was used instead of the inorganic filler B. This organic-inorganic composite filler G was excellent in transparency and was measured for the contact angle. The result was 114°.

[Preparation of Organic-Inorganic Composite Filler H]

A uniform paste was prepared by mixing 25 parts by weight of a liquid resin, 2.5 parts by weight of Aerosil R711, and 72.5 parts by weight of the inorganic filler B and then uniformly kneading. The liquid resin was a mixture consisting of 56.4 parts by weight of UDMA, 28.2 parts by weight of Bis-MPEPP, 9.4 parts by weight of 3G, 6 parts by weight of TEOS, and 0.5 part by weight of BPO. The paste was cured by heating for 4 hours at 100° C. under a nitrogen atmosphere, and grinded and classified to obtain a powder having 25 μm average particle diameter. Further, surface treatment was performed for 100 parts by weight of the powder with 6 parts by weight of MPS in accordance with an ordinary method to obtain an organic-inorganic composite filler H. This organic-inorganic composite filler H was excellent in transparency and was measured for the contact angle. The result was 115°.

[Preparation of Organic-Inorganic Composite Filler I]

A uniform paste was prepared by mixing 25 parts by weight of a liquid resin, 2.5 parts by weight of Aerosil R711, and 72.5 parts by weight of the inorganic filler B and then uniformly kneading. The liquid resin was a mixture consisting of 47 parts by weight of UDMA, 47 parts by weight of 3G, 6 parts by weight of TEOS, and 0.5 part by weight of BPO. The paste was cured by heating for 4 hours at 100° C. under a nitrogen atmosphere, and grinded and classified to obtain a powder having 25 μm average particle diameter. Further, surface treatment was performed for 100 parts by weight of the powder with 6 parts by weight of MPS in accordance with an ordinary method to obtain an organic-inorganic composite filler I. This organic-inorganic composite filler I was inferior in transparency and was measured for the contact angle. The result was 115°.

[Preparation of Organic-Inorganic Composite Filler J]

A uniform paste was prepared by mixing 25 parts by weight of a liquid resin, 2.5 parts by weight of Aerosil R711, and 72.5 parts by weight of the inorganic filler B and then uniformly kneading. The liquid resin was a mixture consisting of 50 parts by weight of Bis-GMA, 50 parts by weight of 3G, and 0.5 part by weight of BPO. The paste was cured by heating for 4 hours at 100° C. under a nitrogen atmosphere, and grinded and classified to obtain a powder having 25 μm average particle diameter. Further, surface treatment was performed for 100 parts by weight of the powder with 6 parts by weight of MPS in accordance with an ordinary method to obtain an organic-inorganic composite filler J. This organic-inorganic composite filler J was good in transparency and was measured for the contact angle. The result was 95°.

[Preparation of Organic-Inorganic Composite Filler K]

An organic-inorganic composite filler K was prepared in the same manner as the organic-inorganic composite filler J except that only the inorganic filler A was used instead of the inorganic filler B. This organic-inorganic composite filler K was good in transparency and was measured for the contact angle. The result was 90°.

[Preparation of Organic-Inorganic Composite Filler L]

A uniform paste was prepared by mixing 25 parts by weight of a liquid resin, 2.5 parts by weight of Aerosil R711, and 72.5 parts by weight of the inorganic filler B and then uniformly kneading. The liquid resin was a mixture consisting of 47 parts by weight of Bis-MPEPP, 47 parts by weight of 3G, 6 parts by weight of TEOS, and 0.5 part by weight of BPO. The paste was cured by heating for 4 hours at 100° C. under a nitrogen atmosphere, and grinded and classified to obtain a powder having 25 μm average particle diameter. Further, surface treatment was performed for 100 parts by weight of the powder with 6 parts by weight of MPS in accordance with an ordinary method to obtain an organic-inorganic composite filler L. This organic-inorganic composite filler L was excellent in transparency and was measured for the contact angle. The result was 102°.

[Preparation of Organic-Inorganic Composite Filler M]

An organic-inorganic composite filler M was obtained by the same manner as in the organic-inorganic composite filler A. However, the mixing ration of the liquid resin and the inorganic filler B in the organic-inorganic composite filler M was different from that in the organic-inorganic composite filler A. This organic-inorganic composite filler M was excellent in transparency and was measured for the contact angle. The result was 121°.

[Preparation of Organic-Inorganic Composite Filler N]

An organic-inorganic composite filler N was obtained by the same manner as in the organic-inorganic composite filler A. However, the mixing ration of the liquid resin and the inorganic filler B in the organic-inorganic composite filler N was different from that in the organic-inorganic composite filler A. This organic-inorganic composite filler N was excellent in transparency and was measured for the contact angle. The result was 119°.

[Preparation of Organic-Inorganic Composite Filler O]

An organic-inorganic composite filler O was obtained by the same manner as in the organic-inorganic composite filler A. However, the mixing ration of the liquid resin and the inorganic filler B in the organic-inorganic composite filler O was different from that in the organic-inorganic composite filler A. This organic-inorganic composite filler O was excellent in transparency and was measured for the contact angle. The result was 110°.

[Preparation of Organic-Inorganic Composite Filler P]

An organic-inorganic composite filler P was obtained by the same manner as in the organic-inorganic composite filler A. However, the mixing ration of the liquid resin and the inorganic filler B in the organic-inorganic composite filler P was different from that in the organic-inorganic composite filler A. This organic-inorganic composite filler P was excellent in transparency and was measured for the contact angle. The result was 106°.

Preparation of Dental Curable Composition

Examples 1 to 16 and Comparative Examples 1 to 3

Pasty dental curable compositions (Examples 1 to 16 and Comparative Examples 1 to 3) were prepared by kneading each component according to each ratio shown in Table 2, and defoaming the kneaded material under vacuum.

The prepared dental curable compositions were evaluated for bending strength, consistency, a polymerization volume shrinkage, operability and a surface luster in accordance with an ordinary method. The results are shown in Table 2.

TABLE 1

| Organic-inorganic composite filler No. | (a) Polymerizable monomer (wt. %) | | | (b) Polymerizable monomer (wt. %) Bis- | (c) Polymerization initiator (wt. %) | (e) Silane compound (wt. %) | | | Mixture of (a), (b), (c) and (e) (wt. %) | (d) Inorganic filler (wt. %) | | | |
|---|---|---|---|---|---|---|---|---|---|---|---|---|---|
| | Bis-GMA | UDMA | MPEPP | 3G | BPO | TEOS | MEOS | MPS | | Inorganic filler A | Inorganic filler B | Inorganic filler C | Aerosil R711 |
| A | 47 | — | — | 47 | 0.5 | 6 | — | — | 25 | — | 72.5 | — | 2.5 |
| B | 47 | — | — | 47 | 0.5 | 6 | — | — | 25 | 72.5 | — | — | 2.5 |
| C | 47 | — | — | 47 | 0.5 | — | 6 | — | 25 | — | 72.5 | — | 2.5 |
| D | 47 | — | — | 47 | 0.5 | — | 6 | — | 25 | 72.5 | — | — | 2.5 |
| E | 47 | — | — | 47 | 0.5 | — | — | 6 | 25 | — | 72.5 | — | 2.5 |
| F | 47 | — | — | 47 | 0.5 | — | — | 6 | 25 | 72.5 | — | — | 2.5 |
| G | 47 | — | — | 47 | 0.5 | 6 | — | — | 25 | — | — | 72.5 | 2.5 |
| H | — | 56.4 | 28.2 | 9.4 | 0.5 | 6 | — | — | 25 | — | 72.5 | — | 2.5 |
| I | — | 50 | — | 50 | 0.5 | 6 | — | — | 25 | — | 72.5 | — | 2.5 |
| J | 50 | — | — | 50 | 0.5 | — | — | — | 25 | — | 72.5 | — | 3.5 |
| K | 50 | — | — | 50 | 0.5 | — | — | — | 25 | 72.5 | — | — | 4.5 |
| L | — | — | 47 | 47 | 0.5 | 6 | — | — | 25 | — | 72.5 | — | 5.5 |
| M | 47 | — | — | 47 | 0.5 | 6 | — | — | 10 | — | 87.5 | — | 2.5 |
| N | 47 | — | — | 47 | 0.5 | 6 | — | — | 7.5 | — | 90 | — | 2.5 |
| O | 47 | — | — | 47 | 0.5 | 6 | — | — | 70 | — | 27.5 | — | 2.5 |
| P | 47 | — | — | 47 | 0.5 | 6 | — | — | 72.5 | — | 25 | — | 2.5 |

TABLE 2

| Organic-inorganic composite filler No. | Contact angle (°) | Refractive index nR | Refractive index nD | \|nR-nD\| | Transparency |
|---|---|---|---|---|---|
| A | 112 | 1.53 | 1.53 | 0.00 | A |
| B | 118 | 1.53 | 1.53 | 0.00 | A |
| C | 115 | 1.53 | 1.53 | 0.00 | A |
| D | 114 | 1.53 | 1.53 | 0.00 | A |
| E | 118 | 1.53 | 1.53 | 0.00 | A |
| F | 117 | 1.53 | 1.53 | 0.00 | A |
| G | 114 | 1.53 | 1.53 | 0.00 | A |
| H | 115 | 1.53 | 1.53 | 0.00 | A |
| I | 115 | 1.50 | 1.53 | 0.03 | C |
| J | 95 | 1.53 | 1.53 | 0.00 | B |
| K | 90 | 1.53 | 1.53 | 0.00 | B |
| L | 102 | 1.53 | 1.53 | 0.00 | A |
| M | 121 | 1.53 | 1.53 | 0.00 | A |
| N | 119 | 1.53 | 1.53 | 0.00 | A |
| O | 110 | 1.53 | 1.53 | 0.00 | A |
| P | 106 | 1.53 | 1.53 | 0.00 | A |

TABLE 3

| Examples and Comparative Examples No. | Organic-inorganic composite filler No. | (g) Polymerizable monomer (wt. %) Bis-GMA | UDMA | Bis-MPEPP | 3G | DMABE | CQ | (f) Organic-inorganic composite filler (wt. %) | (f) Organic-inorganic composite filler | (d) Inorganic filler (wt. %) Inorganic filler B | Aerosil R711 | Filling rate of the filler (wt. %) |
|---|---|---|---|---|---|---|---|---|---|---|---|---|
| Example 1 | A | 12 | — | — | 8 | 0.2 | 0.06 | 45 | | 35 | 2 | 80.2 |
| Example 2 | B | 12 | — | — | 8 | 0.2 | 0.06 | 45 | | 35 | 2 | 80.2 |
| Example 3 | C | 12 | — | — | 8 | 0.2 | 0.06 | 45 | | 35 | 2 | 80.2 |
| Example 4 | D | 12 | — | — | 8 | 0.2 | 0.06 | 45 | | 35 | 2 | 80.2 |
| Example 5 | E | 12 | — | — | 8 | 0.2 | 0.06 | 45 | | 35 | 2 | 80.2 |
| Example 6 | F | 12 | — | — | 8 | 0.2 | 0.06 | 45 | | 35 | 2 | 80.2 |
| Example 7 | A | — | — | 12 | 8 | 0.2 | 0.06 | 45 | | 35 | 2 | 80.2 |
| Example 8 | A | 6 | — | — | 4 | 0.1 | 0.03 | 50.6 | | 39.4 | 1 | 90.0 |
| Example 9 | E | 7.2 | — | — | 4.8 | 0.12 | 0.04 | 50 | | 40 | 1.2 | 88.2 |
| Example 10 | G | 12 | — | — | 8 | 0.2 | 0.06 | 45 | | 35 | 2 | 80.2 |
| Example 11 | H | — | 12 | — | 6 | 2 | 0.2 | 0.06 | 45 | 35 | 2 | 80.2 |
| Example 12 | I | — | 12 | — | 6 | 2 | 0.2 | 0.06 | 45 | 35 | 2 | 80.2 |
| Example 13 | M | 12 | — | — | 8 | 0.2 | 0.06 | 45 | | 35 | 2 | 80.2 |
| Example 14 | N | 12 | — | — | 8 | 0.2 | 0.06 | 45 | | 35 | 2 | 80.2 |
| Example 15 | O | 12 | — | — | 8 | 0.2 | 0.06 | 45 | | 35 | 2 | 80.2 |
| Example 16 | P | 12 | — | — | 8 | 0.2 | 0.06 | 45 | | 35 | 2 | 80.2 |
| Comparative Example 1 | J | 12 | — | — | 8 | 0.2 | 0.06 | 45 | | 35 | 2 | 80.2 |
| Comparative Example 2 | K | 12 | — | — | 8 | 0.2 | 0.06 | 45 | | 35 | 2 | 80.2 |
| Comparative Example 3 | L | — | — | 12 | 8 | 0.2 | 0.06 | 45 | | 35 | 2 | 80.2 |

TABLE 4

| Examples and Comparative Examples No. | Organic-inorganic composite filler No. | Filling rate of the filler (wt. %) | Bending strength (Mpa) | Consistency (mm) | Polymerization Volume Shrinkage (vol %) | Operability | Surface Glossiness |
|---|---|---|---|---|---|---|---|
| Example 1 | A | 80.2 | 145 | 19.6 | 1.61 | B | A |
| Example 2 | B | 80.2 | 141 | 19.3 | 1.63 | B | A |
| Example 3 | C | 80.2 | 148 | 20.3 | 1.66 | B | A |
| Example 4 | D | 80.2 | 143 | 19.0 | 1.70 | B | A |
| Example 5 | E | 80.2 | 140 | 20.0 | 1.64 | B | A |
| Example 6 | F | 80.2 | 138 | 19.6 | 1.69 | B | A |
| Example 7 | A | 80.2 | 129 | 18.3 | 1.63 | B | A |
| Example 8 | A | 90.0 | 158 | 15.5 | 0.93 | A | A |
| Example 9 | E | 88.2 | 150 | 16.0 | 1.06 | A | A |
| Example 10 | G | 80.2 | 142 | 19.7 | 1.67 | B | B |
| Example 11 | H | 80.2 | 146 | 18.1 | 1.67 | B | A |
| Example 12 | I | 80.2 | 146 | 20.1 | 1.64 | B | A |
| Example 13 | M | 80.2 | 149 | 20.5 | 1.61 | B | A |
| Example 14 | N | 80.2 | 122 | 20.3 | 1.58 | B | A |
| Example 15 | O | 80.2 | 130 | 18.5 | 1.63 | B | A |
| Example 16 | P | 80.2 | 124 | 18 | 1.68 | B | A |
| Comparative Example 1 | J | 80.2 | 83 | 13.2 | 1.72 | C | A |

TABLE 4-continued

| Examples and Comparative Examples No. | Organic-inorganic composite filler No. | Filling rate of the filler (wt. %) | Bending strength (Mpa) | Consistency (mm) | Polymerization Volume Shrinkage (vol %) | Operability | Surface Glossiness |
|---|---|---|---|---|---|---|---|
| Comparative Example 2 | K | 80.2 | 75 | 12.5 | 1.75 | C | A |
| Comparative Example 3 | L | 80.2 | 105 | 17.3 | 1.69 | B | A |

As shown in Table 4, it was found that the dental curable compositions of Comparative Examples 1 and 2 using a conventional organic-inorganic composite filler containing no silane compound, had a good surface luster of the cured body, but had very low bending strength. In addition, it was found that because of the poor wettability of the organic-inorganic composite filler with respect to the resin, consistency was low, and operability is poor because dry paste property.

Comparative Example 3 did not use the polymerizable monomer having at least one functional group selected from the group consisting of —OH group, —NH— group, and —NH$_2$ group. Therefore, it was found that interaction between the silane compound contained in the organic-inorganic composite filler and the resin decreased, and the bending strength became low.

In contrast, it was found that the dental curable compositions shown in Examples 1 to 16 which use the organic-inorganic composite filler of the present invention (A to I and M to P) have not only excellent paste operability, and an excellent surface luster of the cured body, but significantly high bending strength. Further, the organic-inorganic composite fillers of the present invention (A to I and M to P) had a high consistency which is the index of wettability with respect to resin, therefore it was possible to highly fill the filler as is apparent from Examples 8 and 9. Thus, it was found that polymerization shrinkage of the dental curable composition was greatly suppressed.

In Example 7, the polymerizable monomer different from the polymerizable monomer used for preparing the organic-inorganic composite filler was used in the dental curable composition. Therefore, it was found that as compared with the other examples which use the same polymerizable monomer as that used for the preparation of the organic-inorganic composite filler as the polymerizable monomer of the dental curable composition, compatibility of the organic-inorganic composite filler for the resin was slightly decreased and bending strength and consistency were slightly lower.

In Example 10, the inorganic filler having 1 μm average particle diameter was used as the organic-inorganic composite filler. Therefore, it was found that the surface luster after polishing was slightly inferior as compared to the other examples using the inorganic filler having 0.4 μm average particle diameter.

In Example 14, the content of the inorganic filler in the organic-inorganic composite filler exceeded 90 parts by weight. Thus, because the organic-inorganic composite filler was excessive, the content of the resin which acted as the binder was insufficient and the organic-inorganic composite filler became brittle. Therefore, it was found that the bending strength was slightly inferior as compared to the Example 1.

In Example 15, the content of the inorganic filler in the organic-inorganic composite filler was 30 parts by weight.

Thus, because the content of the inorganic filler was low, surface hydrophobicity became lower. Therefore, it was found that the contact angle and consistency decreased and bending strength was slightly inferior, as compared to the Example 1.

In Example 16, the content of the inorganic filler in the organic-inorganic composite filler was less than 30 parts by weight. Thus, surface hydrophobicity became further lower. Therefore, it was found that the contact angle and consistency more decreased and bending strength was slightly inferior, as compared to the other Examples.

From the above results, it had been confirmed that the dental curable composition of the present invention had an excellent surface luster after polishing, transparency, low polymerization shrinkage, high mechanical strength, and excellent operability.

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty. Accordingly, any such changes and modifications are intended to be included in the scope of the embodiments.

What is claimed is:

1. An organic-inorganic composite filler including a cured body of a mixture containing:
   a polymerizable monomer (a) having at least one functional group selected from the group consisting of —OH group, —NH— group, and —NH$_2$ group,
   a polymerizable monomer (b) having no functional group selected from the group consisting of —OH group, —NH— group, and —NH$_2$ group,
   a polymerization initiator (c),
   an inorganic filler (d), and
   a silane compound (e) which generates —OH group by hydrolysis and is represented by the following formula (1)

(1)

wherein X represents halogen or —NCO, Y represents —OR, wherein R represents H or alkyl group having 1 to 4 carbon atoms, Z represents a saturated hydrocarbon group and/or an unsaturated hydrocarbon group arbitrarily containing hetero atom and having 1 to 20 carbon atoms, $1+m+n=4$, $1=0$ to 3, $m=1$ to 4, and $n=0$ to 3, wherein a content of the silane compound (e) in the mixture is in a range from 1 to 50 parts by weight based on 100 parts by weight of a total weight of the mixture.

2. The organic-inorganic composite filler according to claim 1, wherein,
an average particle diameter of the inorganic filler (d) is in the range from 0.01 to 3.0 μm.

3. The organic-inorganic composite filler according to claim 1, wherein,
the content of the inorganic filler (d) in the organic-inorganic composite filler is in a range from 30 to 90 parts by weight.

4. The organic-inorganic composite filler according to claim 1, wherein,
a relationship between the refractive index "nR" after curing of the resin matrix containing the polymerizable monomer (a), the polymerizable monomer (b), and the polymerization initiator (c) and the refractive index "nD" of the inorganic filler satisfies the following formula (2)

$$0 \leq |nR-nD| < 0.03 \tag{2}.$$

5. The organic-inorganic composite filler according to claim 1, wherein,
the organic-inorganic composite filler is surface treated with a silane coupling agent.

6. A dental curable composition containing
the organic-inorganic composite filler (f) according to claim 5, a polymerizable monomer (g), an inorganic filler (h), and a polymerization initiator (i).

7. The organic-inorganic composite filler according to claim 2, wherein,
the content of the inorganic filler (d) in the organic-inorganic composite filler is in a range from 30 to 90 parts by weight.

8. The organic-inorganic composite filler according to claim 2, wherein,
a relationship between the refractive index "nR" after curing of the resin matrix containing the polymerizable monomer (a), the polymerizable monomer (b), and the polymerization initiator (c) and the refractive index "nD" of the inorganic filler satisfies the following formula (2)

$$0 \leq |nR-nD| < 0.03 \tag{2}.$$

9. The organic-inorganic composite filler according to claim 3, wherein,
a relationship between the refractive index "nR" after curing of the resin matrix containing the polymerizable monomer (a), the polymerizable monomer (b), and the polymerization initiator (c) and the refractive index "nD" of the inorganic filler satisfies the following formula (2)

$$0 \leq |nR-nD| < 0.03 \tag{2}.$$

10. The organic-inorganic composite filler according to claim 2, wherein,
the organic-inorganic composite filler is surface treated with a silane coupling agent.

11. The organic-inorganic composite filler according to claim 3, wherein,
the organic-inorganic composite filler is surface treated with a silane coupling agent.

12. The organic-inorganic composite filler according to claim 4, wherein,
the organic-inorganic composite filler is surface treated with a silane coupling agent.

13. The organic-inorganic composite filler according to claim 7, wherein,
the organic-inorganic composite filler is surface treated with a silane coupling agent.

14. The organic-inorganic composite filler according to claim 8, wherein,
the organic-inorganic composite filler is surface treated with a silane coupling agent.

15. The organic-inorganic composite filler according to claim 9, wherein,
the organic-inorganic composite filler is surface treated with a silane coupling agent.

16. A dental curable composition containing
the organic-inorganic composite filler (f) according to claim 10, a polymerizable monomer (g), an inorganic filler (h), and a polymerization initiator (i).

17. A dental curable composition containing
the organic-inorganic composite filler (f) according to claim 11, a polymerizable monomer (g), an inorganic filler (h), and a polymerization initiator (i).

18. A dental curable composition containing
the organic-inorganic composite filler (f) according to claim 12, a polymerizable monomer (g), an inorganic filler (h), and a polymerization initiator (i).

19. A dental curable composition containing
the organic-inorganic composite filler (f) according to claim 13, a polymerizable monomer (g), an inorganic filler (h), and a polymerization initiator (i).

20. A dental curable composition containing
the organic-inorganic composite filler (f) according to claim 14, a polymerizable monomer (g), an inorganic filler (h), and a polymerization initiator (i).

21. A dental curable composition containing
the organic-inorganic composite filler (f) according to claim 15, a polymerizable monomer (g), an inorganic filler (h), and a polymerization initiator (i).

* * * * *